(12) United States Patent
Thompson

(10) Patent No.: US 8,011,067 B2
(45) Date of Patent: Sep. 6, 2011

(54) KNOB HANDLE FOR TRANSMITTING A TORQUE TO CABLES, TUBES, OR THE LIKE

(75) Inventor: Brian James Thompson, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 481 days.

(21) Appl. No.: 11/942,841

(22) Filed: Nov. 20, 2007

(65) Prior Publication Data

US 2009/0124398 A1    May 14, 2009

(30) Foreign Application Priority Data

Dec. 4, 2006  (EP) .................................... 06024994

(51) Int. Cl.
*G05G 1/06*    (2006.01)
(52) U.S. Cl. ........................................................ 16/441
(58) Field of Classification Search ...................... 16/441, 16/436, 430, 421, 110.1, 433; 600/146–149; 604/528, 95.04; 606/1, 46, 167, 170, 174; 294/15–17, 34, 57; 74/523, 553
See application file for complete search history.

(56) References Cited

U.S. PATENT DOCUMENTS

| | | | | |
|---|---|---|---|---|
| 4,469,109 A * | 9/1984 | Mehl | ............................ | 600/566 |
| 4,793,363 A * | 12/1988 | Ausherman et al. | ........... | 600/567 |
| 5,281,230 A * | 1/1994 | Heidmueller | ................. | 606/127 |
| 5,358,478 A * | 10/1994 | Thompson et al. | ......... | 604/95.04 |
| 5,368,046 A * | 11/1994 | Scarfone et al. | ............... | 600/567 |
| 5,551,945 A * | 9/1996 | Yabe et al. | ..................... | 600/122 |
| 5,676,653 A * | 10/1997 | Taylor et al. | ................ | 604/95.04 |
| 5,860,953 A | 1/1999 | Snoke et al. | | |
| 5,976,121 A * | 11/1999 | Matern et al. | ...................... | 606/1 |
| 6,019,776 A * | 2/2000 | Preissman et al. | ............. | 606/185 |
| 6,030,360 A * | 2/2000 | Biggs | ......................... | 604/95.01 |
| 6,074,343 A | 6/2000 | Nathanson et al. | | |
| 6,162,208 A * | 12/2000 | Hipps | ............................... | 606/1 |
| 2005/0125009 A1* | 6/2005 | Perry et al. | .................... | 606/139 |
| 2006/0252993 A1 | 11/2006 | Freed et al. | | |

OTHER PUBLICATIONS

European Search Report dated Apr. 25, 2007, International Application No. EP06024994.

\* cited by examiner

*Primary Examiner* — Chuck Y. Mah
(74) *Attorney, Agent, or Firm* — Dean L. Garner

(57) ABSTRACT

A handle (10) is suitable for transmitting a torque between a rotation knob and a respective output shaft connectable to cables, tubes, or the like, wherein said handle comprises at least first and second transmission lines which operate between a first rotation knob (12) and a first output shaft (22) and between a second rotation knob (14) and a second output shaft (24), respectively. The first and second rotation knobs are co-axially arranged along a common axis (X). The first and second output shafts are arranged on different axes (X, Y). The handle comprises a lock-out mechanism suitable for selecting between the first transmission line and the second transmission line thus preventing the rotation of the one rotation knob while the other is being rotated. The lock-out mechanism alternatively operates on the one of the rotation knobs, while the other is released due to the relative translation of the knobs along the common axis (XI between a first relative position and a second relative position and vice versa.

10 Claims, 3 Drawing Sheets

KNOB HANDLE FOR TRANSMITTING A TORQUE TO CABLES, TUBES, OR THE LIKE

FIELD OF THE INVENTION

The object of the present invention is a handle suitable for transmitting a torque between a rotation knob and a respective output shaft connectable to cables, tubes, or the like.

Particularly, the present invention relates to a handle suitable for being used as a handle for surgical equipment, such as flexible endoscopic devices that utilize torque transmission to operate the distal end of the flexible device.

More particularly, the present invention relates to a handle that can be defined as being "in-line", i.e. suitable for selectively transmitting a torque between at least first and second rotation knobs that are co-axially arranged along a common axis and at least first and second output shafts that are arranged on different axes.

In particular this invention can be used wherever torque is to be applied through multiple rotation knobs and outputted through multiple cables, tubes, etc

BACKGROUND OF THE INVENTION

Particularly in the surgical field, the need is particularly felt of having handles suitable to transmit a torque between a rotation knob and an output shaft via several transmission lines. This device would be advantageously applied in diagnostic and therapeutic endoscopic procedures that require flexible torque transmission where the provision of small-sized structures operating in a simple and intuitive manner is particularly required.

Handles capable of transmitting torque through multiple transmission lines via a single handle with "in-line" rotation knobs are not presently known.

The problem at the heart of the present invention is thus to provide a handle which has such structural and functional characteristics as to meet said requirements.

SUMMARY OF THE INVENTION

This problem is solved by means of a handle in accordance with claim 1. Particularly, this problem is solved by means of a handle suitable of transmitting a torque between a rotation knob and a respective output shaft connectable to cables, tubes, or the like, wherein said handle comprises at least first and second transmission lines operating between a first rotation knob and a first output shaft, and between a second rotation knob and a second output shaft, respectively, wherein said first and second rotation knobs, are co-axially arranged along a common axis, wherein said first and second output shafts are arranged on different axes, and wherein said handle comprises a lock-out mechanism that is suitable for selecting between said first transmission line and said second transmission line by preventing the rotation of the one knob while the other is being rotated, wherein said lock-out mechanism alternatively operates on the one of the knobs, while the other is released, following the relative translation of the knobs along the common axis between a first relative position and a second relative position, and vice versa.

BRIEF DESCRIPTION OF THE DRAWINGS

Further characteristics and the advantages of the handle according to the invention will become clear from the following description of a preferred embodiment thereof, provided by way of non-limiting example with reference to the appended drawings, in which.

DETAILED DESCRIPTION OF THE INVENTION

With reference to said figures, with 10 has been generally indicated a handle that can be defined as "in-line", i.e. suitable for selectively transmitting a torque between at least first and second rotation knobs that are co-axially arranged along a common axis and at least first and second output shafts that are arranged on different axes and are connectable to cables, tubes, or the like.

In other words the following invention describes a handle capable of transmitting torque through multiple rotation knobs located on a common axis i.e. "In-Line" and outputting torque through multiple axis via cables, tubes, etc. The following also describes a lock-out mechanism that prevents the rotation of one rotation knob while another is rotated. The lock-out mechanism is activated by pushing one rotation knob relative to the other along the common axis.

Figure 1:
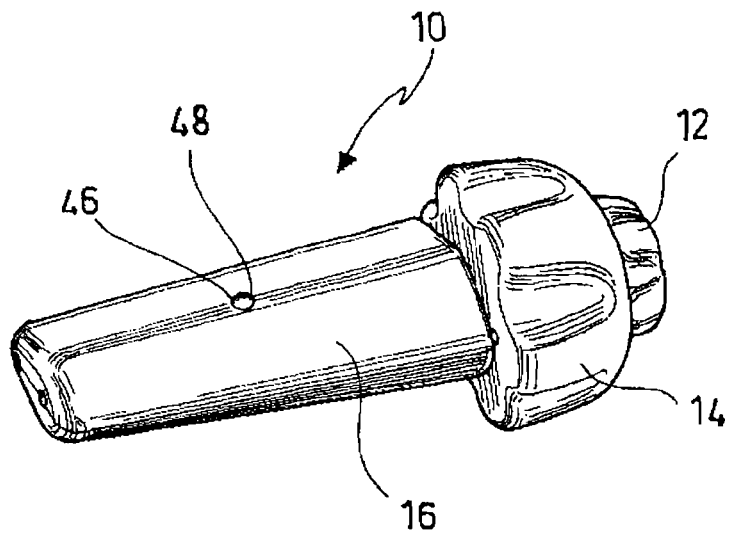
FIG. 1 illustrates a perspective view of a handle according to the present invention.

FIG. 1 illustrates a perspective view of the handle 10 in which the first rotation knob 12 and the second rotation knob 14 are illustrated as being connected to a handle shroud 16. Preferably, the shroud consists of two half-shells, as may be seen in the subsequent figures. In accordance with a possible embodiment, the first rotation knob 12 is externally arranged relative to the second rotation knob 14. Furthermore, the second rotation knob 14 comprises a seat 15 that is suitable for receiving at least one portion of the first rotation knob 12, in a possible relative position of the two knobs.

The subsequent figures illustrate the inner details in which a first tube 18 connected to the first rotation knob 12 and a second tube 20 connected to the second rotation knob 14 are illustrated.

The two rotation knobs are co-axially arranged along a common axis X, and particularly according to what is illustrated in the figures, the second tube 20 is hollow, in order to internally receive at least one portion of the first tube 18. Particularly, the first tube 18 comprises a first portion 18a having such crosswise dimensions as to be inserted within the second tube 20, and a second portion 18b having larger crosswise dimensions than the first portion and the cavity of the second tube, which portion is arranged opposite the first rotation knob 12.

The first tube 18 is connected to a first output shaft 22, and the second tube 20 is connected to a second output shaft 24. In the example illustrated herein, a substantially direct connection is provided between the first tube 18 and the first output shaft 22, whereas the connection between the second tube 20 and the second output shaft 24 is provided by means of at least one gear 26.

Advantageously, the second portion 18b of the first tube 18 has a hollow end suitable for receiving therein a portion 22a of the first output shaft 22.

Generally, the first and second output shafts are arranged on different axes and can be connected to cables, tubes, or the like. In accordance to what is illustrated in the attached figures, the two output shafts are arranged parallel to each other. Particularly, the first output shaft 22 is arranged along the same common axis X as the two rotation knobs and first tube 18, whereas the second output shaft 24 is arranged along a parallel axis Y.

In accordance with the present invention, the handle 10 is suitable for transmitting a torque from the first and second knobs to one of the two output shafts, according to the modes that will be described below. Advantageously, the present handle is suitable for alternatively selecting between a first transmission line operating between the first rotation knob 12 and the first output shaft 22, and a second transmission line operating between the second rotation knob 14 and the second output knob 24, wherein at least one of said transmission lines comprises at least one gear for differentiating the axes of the output shafts.

Advantageously, the handle 10 comprises a lock-out mechanism to prevent a rotation knob from rotating while the other is being rotated. Particularly, the lock-out mechanism alternatively operates on the one of the rotation knobs, while the other is released, following the relative translation of the knobs along the common axis X between a first relative position (FIG. 2) and a second relative position (FIG. 3) and vice versa.

Figure 2:
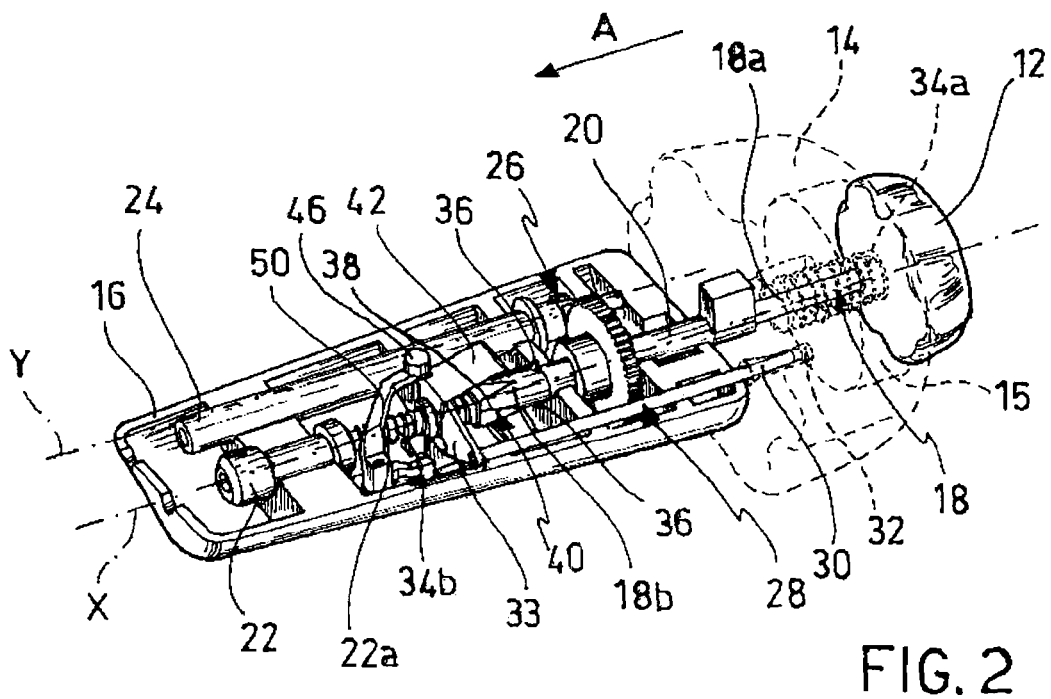
FIG. 2 illustrates the handle in FIG. 1 wherein the shroud has been partially opened and wherein the second knob is shown in phantom in order to better illustrate several components.
Figure 3:
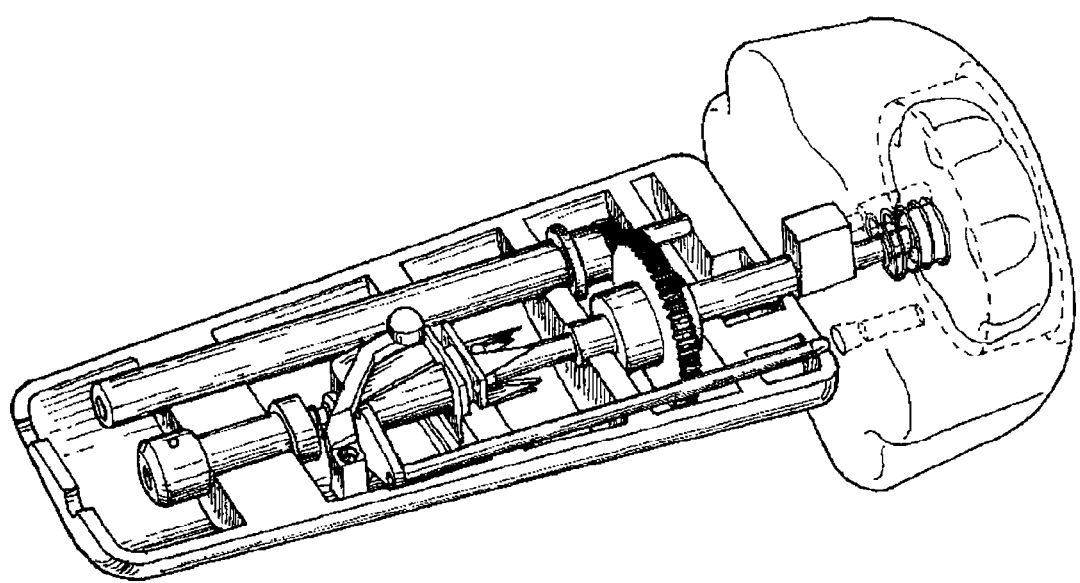
FIG. 3 illustrates the handle in FIG. 2 in a different operating condition.

In accordance with a possible embodiment, the lock-out device comprises a lock-out pin 28 that is connected to the first rotation knob 12 such as to allow the rotation of the first rotation knob 12, and such as to result integral with the first rotation knob during the relative translation of the two knobs. Particularly, the lock-out pin 28 has an end 30 that is suitable for being housed within a seat 32 of the second rotation knob 14 when the two knobs are in the first relative position, such as to lock the rotation of the second rotation knob (FIG. 2). Furthermore, the end 30 is suitable for being disengaged from the seat 32 of the second rotation knob 14 when the two knobs are in the second relative position, in order to allow the rotation of the second knob (FIG. 3).

In accordance with a possible embodiment, the lock-out pin 28 is arranged parallel to the first tube 18 and connected thereto by means of a carriage 33. The carriage 33 is fixed to the lock-out pin 28 and is fastened to the first tube 18 such as to allow the rotation of the first rotation knob 12 and such as to translatably engage the lock-out pin 28 during the relative translation of the knobs.

Resilient elements suitable to maintain and restore the first relative position of said knobs have been designated with 34a and 34b. Particularly, a first resilient element 34a is directly interposed between the first and second rotation knobs, whereas a second resilient element 34b is interposed between the first knob 12 (first tube 18) and the shroud 16 (in the example as illustrated in the figure, the second resilient element 34b is fitted on the portion 22a of the first output shaft).

In accordance with a possible embodiment, the first rotation knob 12 comprises at least a crosswise extension 36 or pin that is suitable for being inserted within a notch 38 of a crown component 40 when the first and second rotation knobs are in the second relative position, in order to prevent the first rotation knob from rotating. Preferably, the crown device 40 is mounted within the handle shroud 16. In accordance with a possible embodiment, for example illustrated therein, two pins 36 are arranged at 180° on the first tube 18.

In accordance with a possible embodiment, the lock-out device can comprise a lock-out spring 42 that is suitable for stopping the relative translation of the first and second rotation knobs in the second relative position. In the embodiment illustrated herein, the lock-out spring 42 is advantageously provided by means of a leaf-spring, having a portion integral with the first tube 18, particularly with the carriage 33. Advantageously, the lock-out spring 42 has two free ends that are arranged at 180° relative to the first tube 18.

Preferably, the shroud 16 of the handle comprises at least one pawl 44 against which the lock-out spring abuts when the two knobs are in the second relative position. In addition, at least one button 46 can be advantageously provided, which is suitable for acting on the spring to disengage the latter from the pawl 44. According to the embodiment illustrated therein, the button 46 extends through an opening 48 of the shroud 16 and has an arm 50 with an end being fixed within the shroud. Preferably, two buttons 46 are provided to be arranged at 180° and respectively suitable for acting on a free end of the lock-out spring 42.

In accordance with a possible embodiment, such as illustrated in the attached figures, the first rotation knob 12 can both rotate about the common axis X and translate relative to the shroud 16 and the second tube 20 between the first relative position (FIG. 2) and the second relative position (FIG. 3). In accordance with a possible embodiment, in the first relative position the first rotation knob 12 is external to the second rotation knob 14, whereas in the second relative position the first rotation knob 12 is at least partially housed within the seat 15 of the second rotation knob 14.

In accordance with the latter embodiment, the second rotation knob 14 can rotate about the common axis X but it is translatably fastened relative to the shroud 16. In this case, in the first relative position, the rotation of the second rotation knob 14 is prevented by the lock-out pin 28 that is translatably integral with the first rotation knob 12, whereas in the second relative position the rotation of the first rotation knob 12 is prevented by the crown component 40 being fixed on the shroud 16.

The operation of a handle such as described above will be described below with particular reference to what is illustrated in the annexed figures, and thus with reference to a second stationary rotation knob that is translatably fastened relative to the shroud, whereas the first rotation knob can both rotate and translate relative to the shroud and second rotation knob. With reference to what is described below, by the term "advance" is meant a translation according to the direction from the rotation knobs to the output shafts, i.e. according to the arrow A in FIG. 2.

The first and second rotation knobs 12, 14 in their initial configuration are located coincident to one another along the common axis of rotation X (FIG. 1). The first rotation knob 12 can be rotated freely while the second rotation knob 14 is locked by the lock-out mechanism. The lock-out pin 28 engages the second rotation knob 14 preventing it to rotate as the first rotation knob 12 is rotated. As the desired rotation is reached by the first rotation knob 12, it can be depressed within the second knob and locked-out such that the first rotation knob 12 can no longer rotate. Simultaneously locking the first rotation knob 12 unlocks the second rotation knob 14 by advancing the lock-out pin 28 such that it no longer engages the second rotation knob 14 (FIG. 3).

The lock-out pin 28 is attached to the lock-out spring 42 and carriage 33 that is connected to the first rotation knob 12 via the first tube 18. As the first rotation knob 12 is depressed into the second rotation knob 14, the lock-out spring 42, carriage 33, and lock-out pin 28 all advance (FIG. 3). Two pins 36 are located 180 degrees from one another on the first tube 18 that connects the first rotation knob 12 to the lock-out spring 42, carriage 33, and lock-out pin 28. As the first rotation knob 12 is depressed and advances forward, these pins 36 engage the crown component 40 that no longer allows rotation of the first rotation knob 12 i.e. locking it out. As stated before, this advances the lock-out pin 28 such that it no longer engages the second rotation knob 14 i.e. allowing for free rotation of the second rotation knob 14 while the first rotation knob 12 is locked-out.

As the first and second rotation knobs are co-axially disposed, the first rotation knob 12 advances within second rotation knob 14.

Figure 4:
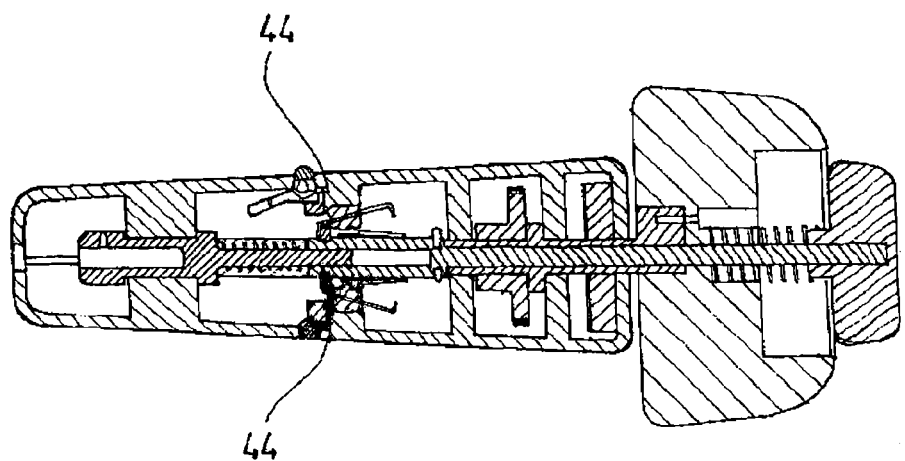
FIG. 4 schematically illustrates a longitudinal section of the handle in FIG. 1.

The lock-out spring 42 in its initial position does not engage the handle shroud 16. This can be seen in FIG. 4.

As the first rotation knob 12 is depressed advancing the lock-out spring 42 forward, the lock-out spring 42 engages the handle shroud 16 not allowing the first rotation knob 12 to retract back to its original position. Two springs are located on the tube 18 connected to the first rotation knob 12 forming the resilient elements 34a and 34b: one spring (34b) is in contact with the lock-out spring 42 and carriage 33 and one spring (34a) is located in contact with the first rotation knob 12 within the second rotation knob 14. These springs provide a resistive force on the first rotation knob 12 as it is depressed as well as allows the first rotation knob 12 to return to its original position when is disengaged.

Figure 5:
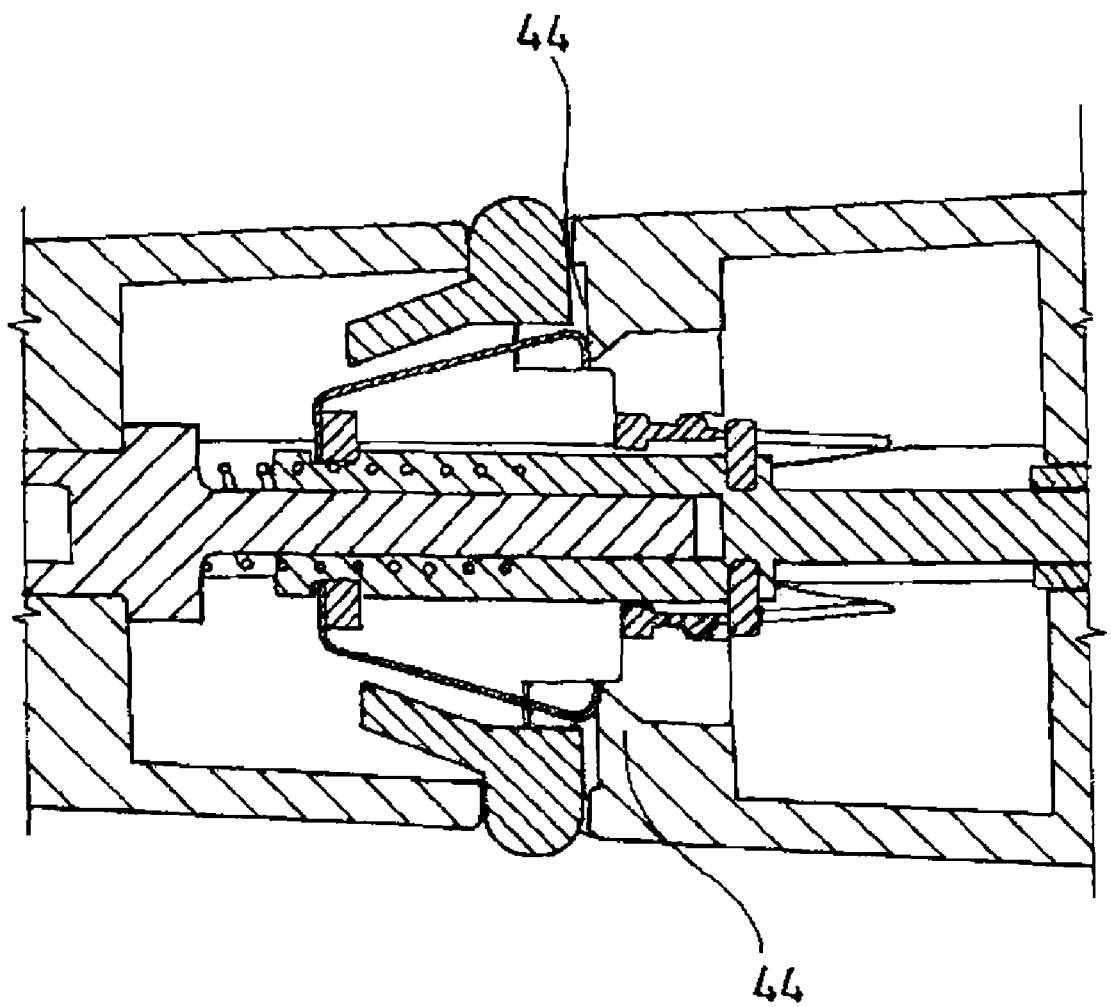
FIG. 5 illustrates an enlarged detail in FIG. 4, in the operative condition of FIG. 3.

When the lock-out spring 42 is engaged with the handle shroud 16, the first rotation knob 16 cannot be retracted back to its original position because the lock-out spring 42 is connected to the carriage 33 and ultimately to the first rotation knob 12. The first rotation knob 12 can only be returned to its original position when the lock-out spring 42 is disengaged allowing the two compression springs (34a, 34b) to act on the first rotation knob 12. The lock-out spring 42 is disengaged by depressing two buttons 46 simultaneously inward against the lock-out spring 42. This can be seen in FIG. 5.

Naturally variants and/or additions may be provided for the embodiment described and illustrated above. For example, it may be provided that the translation of the first knob is prevented, while the translation of the second rotation knob is allowed. Or, it may be provided that both rotation knobs can translate relative to the shroud 16.

In order to satisfy contingent and specific requirements, an expert in the art may apply to the above-described preferred embodiment of the handle many modifications, adaptations and replacements of elements with other functionally equivalent elements without, however, departing from the scope of the following claims.

The invention claimed is:

1. A handle (10) comprising a first rotation knob (12) and a respective first output shaft (22) connectable to a torque transmitter, and a second rotation knob (14) and a respective second output shaft (24) connectable to a torque transmitter, and at least first and second transmission lines suitable for transmitting torque between the first rotation knob (12) and the first output shaft (22) and between the second rotation knob (14) and the second output shaft (24), said first and second transmission lines including a first tube (18) connected between the first rotation knob (12) and the first output shaft (22) and a second tube (20) connected between the second rotation knob (14) and the second output shaft (24),
wherein said first and second rotation knobs are co-axially arranged along a common axis (X) and said first rotation knob (12) is translatable along said common axis (X) relative to said second rotation knob (14) between a first position and a second position,
wherein said first and second output shafts are arranged on different axes (X, Y),
and wherein said handle comprises a lock-out mechanism for selecting between said first transmission line and said second transmission line, said lock-out mechanism comprising a mechanism for preventing the rotation of one of said first and second knobs while allowing the rotation of the other one of said first and second knobs, said mechanism comprising a lock-out pin (28) connected to the first rotation knob (12) via said first tube (18) such that the lock-out pin (28) translates together with the first rotation knob (12) along the common axis (X) and the first rotation knob (12) can rotate about the common axis (X) without rotating the lock-out pin (28), said lock-out pin (28) having an end (30) which engages a seat (32) of the second rotation knob (14) when the first rotation knob (12) is translated in said first relative position, thereby preventing the second rotation knob (12) from rotating, and which end (30) disengages said seat (32) of the second rotation knob (14) when the first rotation knob (12) is translated in said second relative position, thereby allowing the second rotation knob (12) to rotate.

2. The handle according to claim 1, wherein said lock-out pin (28) is arranged parallel to the first tube (18) connected to said first rotation knob.

3. The handle according to claim 1, wherein said first rotation knob (12) comprises at least one crosswise extension or pin (36) suitable for being inserted within a notch (38) of a crown element (40) of the handle when the first rotation knob is translated in said second position relative to the first rotation knob, thereby preventing the first rotation knob from rotating (12).

4. The handle according to claim 3, wherein said crown device (40) is mounted within a shroud (16) of said handle (10).

5. A handle (10) according to claim 1, wherein said lock-out mechanism comprises a lock-out spring (42) connected to the first tube (18) and configured to abut against at least one pawl (44) of the handle when the first rotation knob is translated in the second position relative to the second rotation knob, thereby locking said first and second rotation knobs in said second relative position.

6. The handle according to claim 5, comprising a shroud (16) forming said at least one pawl (44) against which said lock-out spring (42) is abutted in said second relative position of said rotation knobs.

7. The handle according to claim 6, comprising at least one button (46) suitable for acting on said lock-out spring (42) in order to disengage the latter from said at least one pawl (44).

8. The handle according to claim 5, wherein said first and second rotation knobs are connected to said first and second tubes (18, 20), respectively, which are co-axially arranged, the one of said tubes being hollow in order to receive the other of said tubes.

9. The handle according to claim 1, wherein the first and second output shafts (22, 24) are arranged at a distance to each other and said first and second rotation knobs are directly connected to said co-axially arranged first and second tubes (18, 20), respectively, and wherein at least one of said first and second tubes (18, 20) is connected by at least one gear (26) to the corresponding one of the first and second output shafts (22, 24).

10. The handle according to claim 1, wherein the second rotation knob (14) comprises a seat (15) that is suitable for receiving at least one portion of the first rotation knob (12), and
wherein in said first relative position the first rotation knob (12) is arranged outside the second rotation knob (14) and in said second relative position the first rotation knob (12) is arranged at least partially inside said seat (15) of the second rotation knob (14).

* * * * *